United States Patent
Drobyshev et al.

(10) Patent No.: US 11,731,918 B2
(45) Date of Patent: Aug. 22, 2023

(54) METHOD FOR PRODUCING BUTADIENE FROM ETHANOL WITH OPTIMISED IN SITU REGENERATION OF THE CATALYST OF THE SECOND REACTION STEP

(71) Applicants: IFP Energies nouvelles, Rueil-Malmaison (FR); COMPAGNIE GENERALE DES ETABLISSEMENTS MICHELIN, Clermont-Ferrand (FR)

(72) Inventors: Kirill Drobyshev, Rueil-Malmaison (FR); Rejane Dastillung, Rueil-Malmaison (FR); Jean-Christophe Gabelle, Rueil-Malmaison (FR); Matthieu Rolland, Rueil-Malmaison (FR)

(73) Assignees: IFP Energies nouvelles, Rueil-Malmaison (FR); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 17/415,811

(22) PCT Filed: Dec. 13, 2019

(86) PCT No.: PCT/EP2019/085113
§ 371 (c)(1),
(2) Date: Jun. 18, 2021

(87) PCT Pub. No.: WO2020/126920
PCT Pub. Date: Jun. 25, 2020

(65) Prior Publication Data
US 2022/0048833 A1 Feb. 17, 2022

(30) Foreign Application Priority Data
Dec. 21, 2018 (FR) ........................... 1873771

(51) Int. Cl.
*C07C 1/207* (2006.01)
*B01J 8/04* (2006.01)
*B01J 19/24* (2006.01)
*B01J 19/14* (2006.01)
*B01J 21/08* (2006.01)
(Continued)

(52) U.S. Cl.
CPC ............... *C07C 1/2072* (2013.01); *B01J 8/04* (2013.01); *B01J 19/14* (2013.01); *B01J 19/2445* (2013.01);
(Continued)

(58) Field of Classification Search
None
See application file for complete search history.

(56) References Cited

U.S. PATENT DOCUMENTS 2,357,365 A  9/1944 Van Horn et al.
2,915,570 A  12/1959 Busch-Petersen et al.
(Continued)

FOREIGN PATENT DOCUMENTS

FR  1294619 A   5/1962
FR  3026100 A1  3/2016
(Continued)

OTHER PUBLICATIONS

Burla et al. "Two-Step Production of 1,3-butadiene from ethanol" Senior Design Reports. University of Pennsylvania (2012). (Year: 2012).*
(Continued)

*Primary Examiner* — In Suk C Bullock
*Assistant Examiner* — Alyssa L Cepluch
(74) *Attorney, Agent, or Firm* — Millen White Zelano and Branigan, PC; Csaba Henter (57) ABSTRACT

The present invention relates to a process for producing butadiene from ethanol, in two reaction steps, comprising a step a) of converting ethanol into acetaldehyde and a step b) of conversion into butadiene, said step b) simultaneously implementing a reaction step and a regeneration step in (n+n/2) fixed-bed reactors, n being equal to 4 or a multiple
(Continued)

thereof, comprising a catalyst, said regeneration step comprising four successive regeneration phases, said step b) also implementing three regeneration loops.

20 Claims, 1 Drawing Sheet

(51) Int. Cl.
  *B01J 23/20* (2006.01)
  *B01J 23/72* (2006.01)
  *B01J 38/04* (2006.01)
  *C07C 45/00* (2006.01)
(52) U.S. Cl.
  CPC ............... *B01J 21/08* (2013.01); *B01J 23/20* (2013.01); *B01J 23/72* (2013.01); *B01J 38/04* (2013.01); *C07C 45/002* (2013.01); *B01J 2219/00164* (2013.01); *C07C 2521/08* (2013.01); *C07C 2523/72* (2013.01)

(56) References Cited

U.S. PATENT DOCUMENTS

| | | |
|---|---|---|
| 9,950,969 B2 | 4/2018 | Dastillung et al. |
| 10,358,396 B2 | 7/2019 | Dastillung et al. |
| 2018/0208522 A1 | 7/2018 | Cadran et al. |
| 2021/0214622 A1 | 7/2021 | Engelman et al. |

FOREIGN PATENT DOCUMENTS

| | | |
|---|---|---|
| FR | 3026101 A1 | 3/2016 |
| FR | 3038851 A1 | 1/2017 |
| WO | 17091771 A2 | 6/2017 |

OTHER PUBLICATIONS

International Search Report PCT/EP2019/085113 dated Mar. 16, 2020 (pp. 1-2).

* cited by examiner

METHOD FOR PRODUCING BUTADIENE FROM ETHANOL WITH OPTIMISED IN SITU REGENERATION OF THE CATALYST OF THE SECOND REACTION STEP

TECHNICAL FIELD

The invention relates to a process for producing butadiene from ethanol operating in two reaction steps, a first step of converting ethanol into acetaldehyde and a second step of converting a mixture of ethanol and acetaldehyde into butadiene, this second step being carried out in several reactors functioning in parallel, in the presence of a catalyst regenerated in situ.

PRIOR ART

Processes for producing butadiene from ethanol were developed in particular by the Russians on the basis of the studies by Lebedev in the 1920s (one-step reaction process) and by the Americans during the Second World War from the studies by Ostromilenski (two-step reaction process: dehydrogenation of ethanol to acetaldehyde, then production of butadiene from an ethanol/acetaldehyde mixture). This two-step process affords slightly better yields. It was performed during the 1940s in the United States but all the units of this type were shut down for mainly economic reasons.

Processes for producing butadiene from ethanol, in the Lebedev version (one step) or the Ostromilenski version (two steps), have a conversion per step of less than 50%.

Another problem of the process is the production of a wide variety of impurities of all kinds: saturated, unsaturated and aromatic hydrocarbons, but also oxygenated products such as alcohols, phenols, aldehydes, ketones, acids, esters, ethers or acetals.

The reason for this is that the overall reaction for the transformation of ethanol into butadiene hides numerous chemical reactions comprising a dehydrogenation reaction for generating acetaldehyde (I), an aldolization/crotonization reaction of acetaldehyde to crotonaldehyde (II), a Merwein-Pondorff-Verley (MPV) reaction between ethanol and crotonaldehyde (III) and finally a step of dehydration of crotyl alcohol to butadiene (IV).

This multiplicity of chemical reactions is the source of numerous byproducts if the sequence of steps is not performed in the order stated above, notably with the presence of secondary dehydration and condensation reactions. Furthermore, other reactions may take place (such as isomerization, cyclization, Diels-Alder reaction, etc.), further increasing the number of byproducts.

Even if many of the byproducts are entrained with the reaction effluent toward separation/processing units downstream of the reactors, as in the CARBIDE process for the two-step production of 1,3-butadiene, presented in particular in the book "Synthetic Rubber", chapter 4 (W. J. Toussaint and J. Lee Marah), or more recently in the processes of the patents FR 3 026 100 and FR 3 026 101, the catalyst used in particular during the second step for the conversion of the ethanol-acetaldehyde mixture into 1,3-butadiene undergoes a rapid reduction in its activity, notably within a few weeks, or even a few days.

Many recent studies have focused on improving the overall butadiene yield of the process, for instance the studies described in the French patent FR 3 026 100, or on improving the activity and selectivity of the catalysts for the second reaction step (cf. for example FR 3 038 851). More particularly, patent FR 3 026 100 describes a two-step process for producing butadiene from an ethanol feedstock obtained from renewable sources, which makes it possible to remove the impurities while at the same time minimizing the loss of ethanol and acetaldehyde and thus maximizing the overall yield of the process. The process described also makes it possible to limit the consumption of utilities, thus reducing the energy consumption of the process. However, patent FR 3 026 100 is silent as regards a system for regenerating notably the catalyst of the second reaction step.

There are few, if any, studies relating to the regeneration of catalysts for conversion of the ethanol/acetaldehyde mixture into butadiene. It thus appears essential to develop a method for regenerating the catalysts in particular for the second reaction step for conversion of ethanol into butadiene, while at the same time maximizing the butadiene yield.

Patent FR 1 294 619 describes a process for the simultaneous regeneration of a catalyst for a cyclic dehydrogenation system with multiple fixed-bed reactors, the catalyst being regenerated under a stream of air and in the presence of a combustible gas such as natural gas (or an equivalent gas composed of $C_1$-$C_4$ hydrocarbons), without recycling of the regeneration gas.

U.S. Pat. No. 2,357,365 describes a conversion-regeneration process in a multi-reactor system, the reactors functioning in pairs, one being in the operational phase while the second is undergoing regeneration. The regeneration of the catalyst is operated simultaneously in at least two reactors, under a gas stream composed of nitrogen and oxygen in a content of 1-2 mol %, said gas stream circulating in a regeneration loop.

U.S. Pat. No. 2,915,570 describes the regeneration of a catalyst for the conversion of hydrocarbons into butadiene, under a stream of air at at least 540° C., said catalyst being based on chromium on an alumina support.

One of the constraints of the process for converting ethanol into butadiene in two reaction steps is the complexity of the protocol for regeneration in particular of the catalysts for the second step. Specifically, the regeneration protocol, which is well known to those skilled in the art, comprises a sequence of phases of flushing under a stream of inert gas with various oxygen contents. This sequence of phases of flushing different compositions with gas streams becomes a problem that is all the more difficult to solve the shorter the duration of the catalytic cycle of the catalysts, in particular based on tantalum, used for the second step.

The present invention is directed toward solving these regeneration problems without having an impact on the butadiene productivity. More particularly, the present invention is directed toward proposing a process for producing butadiene, in two reaction steps, comprising an optimized method for the in situ regeneration of the catalyst for the second reaction step, said process making it possible to ensure the continuous production of butadiene in a maximized yield and to reduce greatly the fluctuations of the composition leaving the reactors and thus of the flow rate of produced butadiene.

SUMMARY OF THE INVENTION

The invention relates to a process for producing butadiene from ethanol, comprising at least the following steps:

a) a step for converting ethanol into acetaldehyde, to produce an ethanol/acetaldehyde effluent, comprising at least one reaction section (A) fed with a stream comprising ethanol and operated in the presence of a catalyst (Ca);
b) a butadiene conversion step comprising at least one reaction-regeneration section in which are simultaneously implemented a reaction step and a regeneration step, in (n+n/2) fixed-bed reactors, n being an integer equal to 4 or a multiple thereof, said (n+n/2) fixed-bed reactors each comprising at least one fixed bed of a catalyst (Cb), said (n+n/2) fixed-bed reactors functioning in parallel and in sequence so that said reaction step starts in each of said reactors with a time shift equal to a quarter of the catalytic cycle time of said catalyst (Cb), said reaction-regeneration section comprising three regeneration loops, and wherein, at each instant:
  b1) said reaction step is operated in n of said fixed-bed reactors, n being an integer equal to 4 or a multiple thereof, fed at least with a fraction of said ethanol/acetaldehyde effluent obtained from step a), at a temperature of between 300 and 400° C., at a pressure of between 0.1 and 1.0 MPa, and for a time equal to the catalytic cycle time of said catalyst (Cb), to produce a reaction effluent, and
  b2) said regeneration step is operated, in n/2 of said fixed-bed reactors, for a total time equal to half of the catalytic cycle time of said catalyst (Cb), and comprises the following four successive phases:
    i. a stripping phase operated at a temperature of between 300 and 400° C., under a stream of inert gas, said phase i) starting on conclusion of the reaction step b1); and then
    ii. a first combustion phase operated on conclusion of phase i) under a gas stream comprising said inert gas and oxygen in a content of less than or equal to 1 vol % relative to the total volume of said gas stream, at a temperature of between 300 and 450° C.; and then
    iii. a second combustion phase operated on conclusion of the first combustion phase ii) under a gas stream comprising said inert gas and oxygen in a content of greater than or equal to 2 vol % relative to the total volume of said gas stream, at a temperature of between 390 and 550° C.; and then
    iv. a final stripping phase operated at a temperature of between 550° C. and 300° C., under a stream of said inert gas;
said three regeneration loops of said reaction-regeneration section comprising a regeneration loop for the inert gas, a regeneration loop for the gas stream of the first combustion phase ii) and a regeneration loop for the gas stream of the second combustion phase iii).

The process according to the invention, which uses the two-step route for converting ethanol into butadiene, allows the in situ regeneration of the catalyst for the second conversion step. One of the advantages of this in situ regeneration lies in the fact that it can at least partly compensate for the problem of rapid fouling of the catalyst used during the second step. The regeneration of the process according to the invention follows relatively mild operating conditions for removing the coke deposited on the catalyst, thus avoiding premature degradation of the catalyst while at the same time allowing very good regeneration performance, i.e. while permitting efficient combustion of the coke deposited on the catalyst for the second reaction step.

One of the advantages of the process according to the invention lies in the fact that it can ensure the continuous production of butadiene, and does so with low fluctuations of the composition of the effluent produced and thus reduced variations of the flow rate of produced butadiene. Specifically, since it uses a multi-reactor system in particular for the second conversion step, with reactors functioning in parallel, and allows rapid transition in a reactor from the operational mode to the regeneration mode, and conversely from the regeneration mode to the operational mode, the process according to the invention ensures a constant flow rate of the effluent at the outlet of the reaction units and homogenizes the composition of the produced effluent throughout the production. Under the conditions of the process according to the invention, the production of butadiene is ensured continuously.

Although it comprises a continuous reaction-regeneration system, the process according to the invention which includes three regeneration loops also affords a substantial saving in utilities. It makes it possible notably to limit the consumption of inert gas, such as nitrogen, which is recycled at least partly. The process according to the invention also allows economic optimization of the process for producing butadiene from ethanol in two reaction steps.

The process of the present invention may, very advantageously, be integrated into a complex process for converting ethanol into butadiene, comprising one or more separation and/or purification units, making it possible to produce a very pure butadiene and to recover the unconverted or partially converted reagents and to recycle them into the reactors. Such a process is very well described, for example, in French patent FR 3 026 100.

DESCRIPTION OF THE EMBODIMENTS

According to the present invention, the term "multi-reactor system" or "multiple-reactor system" means a set of (n+n/2) fixed-bed reactors, n being an integer equal to 4 or a multiple thereof, or a set of at least six (i.e. 4+2) reactors, functioning in parallel and sequentially, i.e. such that the reaction step, notably reaction step b1), starts in each of the reactors of said multi-reactor system with a time shift relative to each other. Preferably, the multi-reactor system of step b) of the process of the invention therefore comprises six fixed-bed reactors, i.e. the integer n is equal to 4. In practice, in the case where the multi-reactor system of step b) of the process of the invention comprises six reactors (R1, R2, R3, R4, R5 and R6), the reaction step b1) starts first in reactor R1, then in reactor R2 after a certain time, noted as t, then in R3 after the same time t relative to R2, and so on up to reactor R6, the time shifts all being equal to the time shift t between R1 and R2. Since the reaction step b1) and the regeneration step b2) follow each other successively and cyclically in each reactor, the regeneration also starts sequentially in each of the reactors. However, at a given moment, since the reactors function in parallel, the reaction and regeneration steps are simultaneous in the multi-reactor system containing (n+n/2) reactors.

According to the present invention, the fixed-bed reactors are said to be "non-operational" or "in non-operational mode" as soon as the regeneration step b2) starts and up to the end of said regeneration step, in particular up to the end of the final stripping phase iv). Conversely, the fixed-bed reactors are said to be "operational" or "in operational mode" when the reactions for conversion of the ethanol/acetaldehyde mixture into butadiene are performed in said fixed-bed reactors, i.e. as soon as the reaction step b1) starts up to the end of the catalytic cycle of the catalyst (Cb) in said fixed-bed reactors. Very advantageously, during step b) of conversion into butadiene of the process according to the invention, there are simultaneously n fixed-bed reactors in operational mode and n/2 fixed-bed reactors in non-operational mode.

According to the present invention, the term "loop regeneration" means that the regeneration gases of step b2) of the process of the invention are at least partly treated, purified and recycled. Thus, the regeneration step b2) uses three regeneration loops for the regeneration gases. Advantageously, the regeneration step b2) comprises a regeneration loop for the inert gas, a regeneration loop for the gas stream with a low content of oxygen and a regeneration loop for the gas stream with a high content of oxygen. Each regeneration loop preferably comprises a system for treating and purifying the corresponding gas stream. Each regeneration loop may independently comprise a purge for removing any waste resulting from the combustion of coke.

According to the invention, the term "catalytic cycle" of a catalyst, in particular of the catalyst (Cb) of the second reaction step, means the operational phase of said catalyst during which said catalyst fully serves its purpose in the reaction notably for conversion of the ethanol/acetaldehyde mixture into butadiene. Preferably, the catalytic cycle of the catalyst (Cb) corresponds to the operational phase of said catalyst when a minimum of 16 mol %, preferably of 23 mol %, of conversion of ethanol per step on said catalyst (Cb) of the second reaction step (i.e. reaction step b1) of the process according to the invention) is ensured.

According to the present invention, when the temperature is said to be "constant", it is clearly understood that it is the nominal temperature that is constant, the real temperature possibly oscillating around this nominal value.

Similarly, a temperature increase or decrease ramp means that the nominal temperature undergoes a temperature increase or decrease, the real temperatures oscillating around the nominal temperature.

According to the present invention, the expression "between . . . and . . . " means that the limit values of the interval are included in the described range of values. If such were not the case and if the limit values were not included in the range described, such a clarification will be given by the present invention.

Thus, the invention relates to a process for producing butadiene from ethanol in two reaction steps, the second step for converting an ethanol/acetaldehyde mixture into butadiene comprising a sequence of reaction and regeneration steps in a multiple-reactor system, the reactors functioning in parallel and in sequence.

More particularly, the invention relates to a process for producing butadiene from ethanol, comprising at least the following steps:

a) a step for converting ethanol into acetaldehyde, to produce an ethanol/acetaldehyde effluent, comprising at least one reaction section (A) fed with a stream comprising ethanol and operated in the presence of a catalyst (Ca), preferably said step for converting ethanol into acetaldehyde is carried out at a temperature of between 200 and 500° C., preferentially between 250° C. and 300° C., and at a pressure of between 0.1 and 1.0 MPa, preferentially between 0.1 and 0.5 MPa, more preferably between 0.1 and 0.3 MPa;

b) a butadiene conversion step comprising at least one reaction-regeneration section in which are simultaneously implemented a reaction step and a regeneration step in (n+n/2) fixed-bed reactors, n being an integer equal to 4 or a multiple thereof, said (n+n/2) fixed-bed reactors each comprising at least one fixed bed of a catalyst (Cb), preferably based on tantalum, said (n+n/2) fixed-bed reactors functioning in parallel and in sequence so that said reaction step starts in each of said reactors with a time shift equal to a quarter of the catalytic cycle time of said catalyst (Cb), said reaction-regeneration section comprising three regeneration loops, and wherein, at each instant:

b1) said reaction step is operated in n of said fixed-bed reactors, n being an integer equal to 4 or a multiple thereof, fed at least with a fraction of said ethanol/acetaldehyde effluent obtained from step a), at a temperature of between 300 and 400° C., preferably between 300 and 360° C., at a pressure of between 0.1 and 1.0 MPa, preferably between 0.2 and 0.4 MPa, and for a time equal to the catalytic cycle time of said catalyst (b), to produce a reaction effluent, and b2) said regeneration step is operated, in n/2 of said fixed-bed reactors, which are advantageously non-operational, for a total time equal to half of the catalytic cycle time of said catalyst (Cb), and comprises, preferably consists of, the following four successive phases:

i. a stripping phase operated at a temperature of between 300 and 400° C., preferably between 330 and 370° C., under a stream of inert gas, preferably of nitrogen, of carbon dioxide ($CO_2$) or mixtures thereof, and very preferably under a stream of nitrogen, advantageously at a flow rate of between 0.5 and 1.5 $Nm^3$/h/kg of catalyst, preferably equal to 1 $Nm^3$/h/kg of catalyst, said phase i) starting on conclusion of the reaction step b1); and then ii. a first combustion phase operated on conclusion of phase i), under a gas stream comprising said inert gas and oxygen (in particular in the form of dioxygen $O_2$) in a content of less than or equal to 1 vol % relative to the total volume of said gas stream, preferably in a content of between 0.1 and 1 vol %, preferentially between 0.3 and 0.7 vol % relative to the total volume of said gas stream, at a temperature of between 300 and 450° C., preferably between 330 and 430° C., in particular at a constant temperature of between 330 and 370° C. followed by a temperature increase ramp of 10 to 30° C./h and then a phase at a constant temperature of between 390 and 430° C., and advantageously at a flow rate of said gas stream of between 1.7 and 2.5 $Nm^3$/h/kg of catalyst, preferably between 1.9 and 2.3 $Nm^3$/h/kg of catalyst; and then iii. a second combustion phase operated on conclusion of the first combustion phase ii), under a gas stream comprising said inert gas and oxygen (in particular in the form of dioxygen $O_2$) in a content of greater than or equal to 2 vol % relative to the total volume of said gas stream, preferably in a content of between 2 and 20 vol %, preferentially between 2 and 10 vol %, more preferentially between 4 and 8 vol % relative to the total volume of said gas stream, at a temperature of between 390 and 550° C., preferably at a constant temperature of between 390 and 430° C. followed by a temperature increase ramp of 10 to 30° C./h and then a phase at a constant temperature of between 460 and 510° C., and advantageously at a flow rate of said gas stream of between 1.2 and 1.8 $Nm^3$/h/kg of catalyst, preferably between 1.35 and 1.50 $Nm^3$/h/kg of catalyst; and then iv. a final stripping phase operated at a temperature of between 550 and 300° C., preferably on a temperature decrease ramp of 50 to 150° C./h followed by a phase at a constant temperature of between 300 and 400° C., preferably between 330 and 370° C., under a stream of said inert gas, preferably of nitrogen, of carbon dioxide ($CO_2$) or mixtures thereof, and very preferably under a stream of nitrogen, advantageously at a flow rate of between 0.5 and 1.5 $Nm^3/h/kg$ of catalyst, preferably equal to 1 $Nm^3/h/kg$ of catalyst;

said three regeneration loops of said reaction-regeneration section comprising a regeneration loop for the inert gas, a regeneration loop for the gas stream of the first combustion phase ii) and a regeneration loop for the gas stream of the second combustion phase iii).

Preferably, the process according to the invention comprises the succession, in particular in this order, of step a) for converting ethanol into acetaldehyde and of step b) of conversion into butadiene, without an intermediate step.

Very advantageously, the process according to the invention may be integrated into a more global process for converting ethanol into butadiene, in particular comprising separation and purification steps downstream of the conversion reactors, for example such as the process described in French patent FR 3 026 100.

The Feedstock

In accordance with the invention, the process converts ethanol into butadiene.

Advantageously, the stream comprising the ethanol which feeds the process according to the invention comprises at least 80% by weight of ethanol, preferentially at least 90% by weight, and preferably at least 93% by weight. Very preferably, the ethanol feedstock comprising said stream meets the EN 15376 fuel ethanol specifications. Said ethanol feedstock may originate from any fossil, plant or animal origin, and in particular from processes for producing ethanol from plant resources.

Step a) for Converting Ethanol into Acetaldehyde

In accordance with the invention, the process comprises a step a) for converting ethanol into acetaldehyde, to produce an ethanol/acetaldehyde effluent, advantageously in liquid form. Said step a) of the process according to the invention comprises at least one reaction section (A) fed with a stream comprising ethanol.

Said step a) for converting ethanol into acetaldehyde is operated in the presence of a catalyst (Ca), advantageously of an alcohol dehydrogenation catalyst. Any catalyst, notably any catalyst for the dehydrogenation of alcohols, in particular of ethanol, known to those skilled in the art may be used in step a) of the process according to the invention. Very preferably, the catalyst (Ca) of said step a) of the process according to the invention is an ethanol dehydrogenation catalyst comprising a dehydrogenating element, more particularly a copper element, more preferentially a copper oxide or a mixture of chromium oxide and copper oxide, and a matrix in particular based on silica.

Advantageously, step a) of the process of the invention is operated under temperature and pressure conditions known to those skilled in the art. Preferably, the reaction section (A) of step a) of the process of the invention is operated at a temperature of between 200 and 500° C., preferentially between 250° C. and 300° C., and at a pressure of between 0.1 and 1.0 MPa, preferentially between 0.1 and 0.5 MPa, more preferably between 0.1 and 0.3 MPa.

Said step a) of the process according to the invention makes it possible advantageously to convert ethanol into acetaldehyde by dehydrogenation of ethanol. Preferably, the conversion of ethanol into acetaldehyde is between 25% and 40% per step, with a selectivity of between 85% and 100% toward acetaldehyde, preferably between 90% and 97% toward acetaldehyde.

In addition to acetaldehyde, the dehydrogenation reaction that is performed during step a) of the process according to the invention produces hydrogen. Thus, preferably, step a) of the process of the invention further comprises a separation section for separating at least one hydrogen effluent in gaseous form and said ethanol/acetaldehyde effluent in liquid form. When it is integrated into said step a) of the process according to the invention, said optional separation section uses gas/liquid separation means known to those skilled in the art. Preferably, said separation section comprises a gas/liquid separator operated at a pressure of between 0.1 and 0.3 MPa and at a temperature of between 25 and 60° C.

Step b) of Conversion into Butadiene

In accordance with the invention, step b) of conversion into butadiene of the process of the invention comprises at least one reaction-regeneration section in which a reaction step and a regeneration step are implemented simultaneously. Said reaction-regeneration section comprises a multiple-reactor system comprising (n+n/2) fixed-bed reactors, n being an integer equal to 4 or a multiple thereof, n preferably being an integer equal to 4, wherein said (n+n/2) fixed-bed reactors function in parallel and in sequence. Said reaction-regeneration section also comprises three regeneration loops and preferably a system of lines and of valves for circulating the regeneration gas streams in each of the (n+n/2) reactors of said reaction-regeneration section. More particularly, said reaction-regeneration section comprises a regeneration loop for the inert gas and two regeneration loops for gas streams comprising oxygen.

If, at a given moment, said reaction step b1) and regeneration step b2) are implemented simultaneously in said multiple-reactor system, i.e. in all of the (n+n/2) fixed-bed reactors of said reaction-regeneration section, they are implemented successively and cyclically in each of said fixed-bed reactors.

In accordance with the invention, step b) is a step for converting an ethanol and acetaldehyde mixture into butadiene, said mixture comprising at least a fraction of said ethanol/acetaldehyde effluent obtained from step a).

According to the invention, each fixed-bed reactor comprises at least one fixed bed of a catalyst (Cb). Said catalyst (Cb) advantageously comprises an element selected from the group consisting of tantalum, zirconium and columbium (or niobium), preferably in their oxide form. Preferably, the catalyst (Cb) comprises the element tantalum, and preferably a tantalum oxide. Advantageously, the catalyst (Cb) also comprises a support, preferably a mesoporous matrix, preferably based on silica. For example, said catalyst (Cb) is the catalyst described in patent application FR 3 038 851. The catalytic cycle time of said catalyst (Cb) is in particular greater than or equal to 1 day, preferably greater than or equal to 6 days, and less than or equal to 20 days, more particularly less than or equal to 15 days. For example, the cycle time of the catalyst (Cb) of the process according to the invention is equal to 10 days. This time makes it possible to ensure an ethanol conversion per step on said catalyst (Cb) at least equal to 16 mol %, preferably at least equal to 23 mol %.

The functioning in sequence of said (n+n/2) reactors, i.e. the functioning time shift of said reactors, is adjusted so that the reaction step b1) starts in each of said reactors with a time shift equal to a quarter of the catalytic cycle time of said catalyst (Cb), so that the reaction step b1) starts in the reactor $R_{i+1}$ with a time shift equal to a quarter of the catalytic cycle time of said catalyst (Cb) relative to the reactor $R_i$, with i being an integer ranging from 1 to ((n+n/2)−1). For example, in the case where the multi-reactor system comprises six reactors (4+2 reactors) and in which the catalytic cycle time is 10 days, the reaction step b1) starts first in reactor R1, then in reactor R2 2.5 days after having started in reactor R1, then in reactor R3 2.5 days after having started in reactor R2, then in reactor R4 2.5 days after having started in reactor R3, and so on up to reactor R6.

In accordance with the invention, step b) comprises a reaction step b1) to produce a reaction effluent, advantageously comprising butadiene.

Advantageously, said fixed-bed reactors used in said reaction step b1) according to the invention, i.e. said operational reactors, are fed with at least a fraction of said ethanol/acetaldehyde effluent obtained from step a). Optionally, said operational fixed-bed reactors used in said reaction step b1) according to the invention may also be fed with a supply of ethanol, notably comprising a recycled ethanol stream, and/or a supply of acetaldehyde, notably comprising a recycled acetaldehyde stream, said recycled acetaldehyde and ethanol streams being obtained from purification-separation units that may be present downstream of the process according to the invention, and in which the unconverted reagents (ethanol, acetaldehyde) are advantageously separated. When said reaction step b1) according to the invention comprises an additional supply of ethanol and/or of acetaldehyde, said feed flow rates of said reaction step b1), in particular in said at least a fraction of said ethanol/acetaldehyde effluent obtained from step a) and in the optional supplies of ethanol and of acetaldehyde, are advantageously adjusted so that the mole ratio between the total molar amount of ethanol relative to the total molar amount of acetaldehyde at the inlet of the operational fixed-bed reactors of said reaction step b1) is between 1 and 5, preferably between 2 and 4 and very preferably between 2.4 and 3.6.

According to the invention, said reaction step b1) is carried out in n of said fixed-bed reactors, n being an integer equal to 4 or a multiple thereof, functioning in parallel and in sequence.

Advantageously, said reaction step b1) is operated at a temperature of between 300 and 400° C., preferably between 300 and 360° C., at a pressure of between 0.1 and 1.0 MPa, preferably between 0.2 and 0.4 MPa, and for a time equal to the catalytic cycle time of said catalyst (Cb). Preferably, said reaction step b1) is operated at a weight hourly space velocity (WHSV) of between 0.8 and 2.5 h$^{-1}$, preferably between 0.8 and 2 h$^{-1}$, the weight hourly space velocity (WHSV, weight per weight per hour) being defined as the ratio between the mass flow rate of ethanol/acetaldehyde feedstock entering the n operational reactors and the mass of catalyst included in said n operational reactors.

Advantageously, said reaction step b1) makes it possible to convert at least a portion of the ethanol/acetaldehyde mixture into butadiene. The butadiene selectivity of this reaction step is preferably greater than 60%, preferably greater than 70%, very preferably greater than 80%. The term "butadiene selectivity" means the mole ratio of the flow rate of butadiene in the reaction effluent obtained from said reaction step b1) to the flow rate of the mixture of ethanol and acetaldehyde consumed in said reaction step b1), expressed as a percentage. The conversion of the ethanol/acetaldehyde mixture is preferably greater than 20%, preferably greater than 25%, preferably greater than 30%. The term "conversion of the ethanol/acetaldehyde mixture" means the mole ratio between the molar flow rate of ethanol and acetaldehyde consumed in said reaction step b1), i.e. the difference in molar flow rate of the ethanol/acetaldehyde mixture between the feed and the reaction effluent obtained from said reaction step b1), and the molar flow rate of the ethanol/acetaldehyde mixture in the feed of said reaction step b1), expressed as a percentage. Preferably, at least 35%, preferably between 35% and 80%, very preferably between 40% and 80% of the acetaldehyde is converted in said reaction section.

Optionally, step b) of the process according to the invention may further comprise a separation section for separating the reaction effluent obtained from the reaction step b1) into at least a gaseous effluent and a liquid effluent. Said separation section uses gas/liquid separation means known to those skilled in the art. The gas/liquid separator preferably used is a separator operated at a pressure of between 0.1 and 0.3 MPa, and a temperature of between 25 and 60° C. Preferably, said gaseous effluent is treated subsequent to said process according to the invention to produce a stream of purified butadiene and the liquid effluent is treated to produce notably a stream rich in unconverted ethanol and/or a stream rich in acetaldehyde. Said stream rich in unconverted ethanol may be advantageously recycled upstream of step a) for converting ethanol into acetaldehyde and/or upstream of step b) for conversion into butadiene, on conclusion of step a). Said stream rich in acetaldehyde may be advantageously recycled upstream of step b) and on conclusion of step a) of the process of the invention.

In accordance with the invention, said reaction-regeneration section of step b) for conversion into butadiene comprises a step b2) of regeneration, in particular of loop regeneration, in the non-operational fixed-bed reactors. At a given moment, n/2 of said fixed-bed reactors of said reaction-regeneration section are non-operational. In each reactor of said reaction-regeneration section, said step b2) is operated on conclusion of reaction step b1), for a time equal to half of the catalytic cycle time of said catalyst (Cb). For example, when the catalytic cycle time of the catalyst (Cb) is 10 days, the duration of the regeneration step b2) is 5 days.

Said regeneration step b2) is an in situ regeneration of the catalyst (Cb) used during the second reaction step for transformation of ethanol into butadiene, i.e. used during reaction step b1) of the process according to the invention. It is known that this second reaction step (step of conversion of an ethanol/acetaldehyde mixture into butadiene) involves a plurality of chemical reactions which may be the source of many byproducts and thus of rapid fouling of the catalyst. Thus, the catalytic cycle of the catalyst (Cb), in particular based on tantalum, of this second reaction step is generally relatively short, notably less than or equal to 20 days, more particularly less than or equal to 15 days, for example equal to 10 days, and the amount of coke deposited on said catalyst at the end of the catalytic cycle is relatively large. Thus, in situ regeneration, preferably loop regeneration, of the catalyst (Cb) in the multiple reactors of step b) of the process according to the invention appears essential to ensure the continuous production of butadiene, while at the same time limiting the consumption of utilities, in particular of the inert gas, such as nitrogen, required in large amounts notably to limit the exothermicity of the burning of the coke, during the regeneration step.

In accordance with the invention, step b2) of regeneration of the catalyst (Cb) comprises, preferably consists of, four successive phases operated in the n/2 non-operational fixed-bed reactors.

First there is a stripping phase i) which starts, in a fixed-bed reactor, on conclusion of the reaction step b1). Said stripping step i) is operated at a temperature of between 300 and 400° C., preferably between 330 and 370° C., very preferably between 340° C. and 360° C., under a stream of inert gas. The inert gas is nitrogen, carbon dioxide ($CO_2$) or mixtures thereof, and preferably nitrogen. Advantageously, the flow rate of inert gas is between 0.5 and 1.5 $Nm^3/h/kg$ of catalyst and is preferably equal to 1 $Nm^3/h/kg$ of catalyst. Very preferably, this stripping phase i) lasts between 2% and 20%, preferably between 5% and 15%, of the total duration of said regeneration step b2), i.e. between 1% and 10%, preferably between 3% and 7%, of the catalytic cycle time of the catalyst (Cb) for step b) of the process according to the invention.

This initial stripping phase i) is followed by a first combustion phase ii), said to be under low $O_2$ conditions, during which the soft coke is calcined. The term "soft coke" means the coke compounds deposited on the catalyst which have a relatively low degradation temperature, in particular below 400° C., for instance compounds resulting from the oligomerization of olefins, notably C4 olefins. During the first combustion phase ii), there may also be a start of calcination of the hard coke, which gathers the hydrocarbon-based compounds with a higher degradation temperature, in particular greater than or equal to 400° C. and less than or equal to 450° C. Said first combustion phase ii) is operated under a gas stream comprising said inert gas and oxygen (in the form of $O_2$) in a content of less than or equal to 1 vol % relative to the total volume of said gas stream, preferably in a content of between 0.1 and 1 vol %, preferentially between 0.3 and 0.7 vol % relative to the total volume of said gas stream. Said first combustion phase ii) is advantageously operated at a temperature of between 300 and 450° C., preferably between 330 and 430° C., in particular at a constant temperature of between 330 and 370° C. followed by a temperature increase ramp of 10 to 30° C./h and then a phase at a constant temperature of between 390 and 430° C. Advantageously, the flow rate of said gas stream, comprising the inert gas and oxygen (in the form of $O_2$) in a content of less than or equal to 1 vol %, is between 1.7 and 2.5 $Nm^3/h/kg$ of catalyst, preferably between 0.9 and 2.3 $Nm^3/h/kg$ of catalyst. Very preferably, said first combustion phase ii) lasts between 5% and 40%, preferably between 10% and 30%, of the total duration of said regeneration step b2), i.e. between 2% and 20%, preferably between 5% and 15%, of the catalytic cycle time of the catalyst (Cb) for step b) of the process according to the invention.

A second combustion phase iii), said to be under high $O2$ conditions, is carried out on conclusion of the first combustion phase ii) to burn off the residual coke, i.e. the coke compounds with the highest degradation temperatures, notably greater than 450° C. Said second combustion phase iii) is operated under a gas stream comprising said inert gas and oxygen (in the form of $O_2$) in a content of greater than or equal to 2 vol % relative to the total volume of said gas stream, preferably in a content of between 2 and 20 vol %, preferentially between 2 and 10 vol %, more preferentially between 4 and 8 vol %, relative to the total volume of said gas stream. Said second combustion phase iii) is advantageously operated at a temperature of between 390 and 550° C., preferably at a constant temperature of between 390 and 430° C. followed according to a temperature increase ramp of 10 to 30° C./h and then a phase at a constant temperature of between 460 and 510° C. Advantageously, the flow rate of said gas stream, comprising the inert gas and oxygen (in the form of $O_2$) in a content of greater than or equal to 2 vol %, is between 1.2 and 1.8 $Nm^3/h/kg$ of catalyst, preferably between 1.35 and 1.50 $Nm^3/h/kg$ of catalyst. Very preferably, said second combustion phase iii) lasts between 5% and 40%, preferably between 10% and 30%, of the total duration of said regeneration step b2), i.e. between 2% and 20%, preferably between 5% and 15%, of the catalytic cycle time of the catalyst (Cb) for step b) of the process according to the invention.

Finally, the regeneration step b2) comprises a final stripping phase iv), carried out on conclusion of the second combustion phase iii), in each of said n/2 fixed-bed reactors, in particular non-operational reactors, under a stream of said inert gas, preferably of nitrogen, of carbon dioxide ($CO_2$) or mixtures thereof, and very preferably under a stream of nitrogen, advantageously at a flow rate of between 0.5 and 1.5 $Nm^3/h/kg$ of catalyst, preferably equal to 1 $Nm^3/h/kg$ of catalyst. Said final stripping phase iv) is advantageously operated at a temperature of between 550 and 300° C., preferably on a temperature decrease ramp of 50 to 150° C./h followed by a phase at a constant temperature of between 300 and 400° C., preferably between 330 and 370° C. Very preferably, said final stripping phase iv) lasts between 2% and 20%, preferably between 5% and 15%, of the total duration of said regeneration step b2), i.e. between 1% and 10%, preferably between 3% and 7%, of the catalytic cycle time of the catalyst (Cb) for step b) of the process according to the invention. Advantageously, the stripping phases i) and iv) make it possible to remove the residual combustion products from the reactors before and after the coke combustion.

Said phases i), ii), iii) and iv) of said regeneration step b2) are operated successively and in this order in each of said (n+n/2) fixed-bed reactors, and advantageously on conclusion of the reaction step b1).

On conclusion of the final stripping phase iv) of the regeneration step b2), the fixed-bed reactors which have undergone the regeneration step b2) are considered to be operational and reaction step b1) may advantageously be carried out in these reactors, which are said to be regenerated. Thus, in each of said (n+n/2) fixed-bed reactors of the reaction-regeneration section of the process according to the invention, the reaction step b1) and the regeneration step b2) are implemented successively and advantageously cyclically. In parallel, at a given moment of the process of the invention, the reaction step b1) and the regeneration step b2) are operated simultaneously in the multi-reactor system used in the process according to the invention.

Very advantageously, said reaction-regeneration section of step b) of the process according to the invention comprises three regeneration loops for the gas streams. Preferably, said reaction-regeneration section of step b) of the process according to the invention also comprises a system of lines and of valves for connecting said (n+n/2) fixed-bed reactors to the regeneration loops, to avoid circulation of the regeneration gas streams in the operational reactors and to circulate the gas streams suitable for the regeneration phases of step b2) in the non-operational reactors.

In particular, said reaction-regeneration section of step b) of the process according to the invention comprises three regeneration loops for the gas streams. Each of said regeneration gas streams can thus independently be recovered at the outlet of the non-operational fixed-bed reactors, purged and/or purified to remove the compounds resulting from the coke combustion, for instance CO, $CO_2$ or water, separated and at least partially recycled. Thus, as a function of the regeneration phase, at least a portion of an inert gas stream, very preferably a nitrogen stream, a gas stream with a low content of oxygen (i.e. an $O_2$ content of less than or equal to 1 vol % relative to the total volume of said gas stream) or a gas stream with a high content of oxygen (i.e. an $O_2$ content of greater than or equal to 2 vol % relative to the total volume of said gas stream) may be recovered, treated and recycled. Each regeneration loop preferably comprises a purge and/or a supply of corresponding gas stream.

Preferably, said reaction-regeneration section of step b) advantageously comprises an inert gas regeneration loop to recover, treat and at least partly recycle the gas streams leaving the reactor during the stripping phases i) and iv), and two regeneration loops for gas streams comprising oxygen, to recover, treat and at least partly recycle the gas streams leaving the reactor during the combustion phases ii) and iii), one making it possible to treat and at least partly recycle the gas stream with a low $O_2$ content (less than or equal to 1 vol % relative to the total volume of said gas stream) necessary for the first combustion phase ii) and the other making it possible to treat and at least partly recycle the gas stream with a high $O_2$ content (greater than or equal to 2 vol % relative to the total volume of said gas stream) necessary for the second combustion phase iii).

Thus, the process according to the invention can ensure the continuous production of butadiene, with limited variations in the composition of the reaction effluent and thus low fluctuations in butadiene production (i.e. low fluctuations in the flow rate of butadiene produced), while at the same time limiting the consumption of utilities, in particular the consumption of inert gas such as nitrogen. The process according to the invention also affords economic savings for a process for producing butadiene from ethanol, in two reaction steps, in particular for a more global process of the type described, for example, in patent FR 3 026 100. The Figures incorporated into the present description and the examples that follow are presented as nonlimiting illustrations of the process according to the invention.

EXAMPLES

The following examples are based on simulations of processes incorporating thermodynamic data set up on experimental points.

In each of the following examples, the process described is incorporated into a more global process such as the one described in French patent FR 3 026 100. The ethanol feedstock for the global process is obtained from a renewable source and comprises more than 93% by weight of ethanol. The flow rate of feedstock feeding the global process is adjusted so as to obtain an annual production of 150 kt/year of a butadiene having a purity of between 99.5% and 100% by weight (compatible with the current use of the product), with an annual duration of functioning of the process of 8000 hours.

In the following examples, the term "variation(s) of composition" means the mean amplitude(s) of variation of the weight contents of the compounds of the reaction effluent, over the duration of functioning.

Example 1 (in Accordance)

In this example, the second reaction unit comprises 6 (4+2) fixed-bed reactors and is operated at a weight hourly space velocity (WHSV) of 2 $h^{-1}$. The regeneration section comprises 3 regeneration loops.

The conversion of ethanol into acetaldehyde is carried out in a multitubular reactor comprising a catalyst based on copper oxide on a silica support, at 275° C. and 0.26 MPa. The ethanol/acetaldehyde effluent, which is separated from the hydrogen stream at the reactor outlet, is then sent to the second reaction unit.

Figure 1:
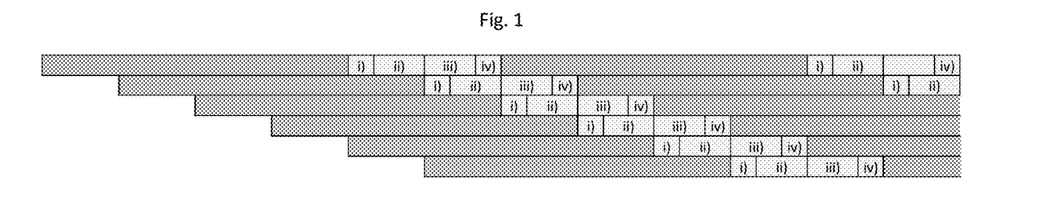
FIG. 1 shows, schematically and in a nonlimiting manner, an operating diagram of fixed-bed reactors in a system containing six fixed-bed reactors, during step b) of conversion into butadiene, a line corresponding to the functioning of a reactor, the steps in dark gray corresponding to the reaction steps b1), the steps in light gray corresponding to the various phases of the regeneration step b2): the phases i) corresponding to the initial stripping phases i), the phases ii) corresponding to the first combustion phases ii), the phases iii) corresponding to the second combustion phases iii) and the phases iv) corresponding to the final stripping phases iv).
Figure 2:
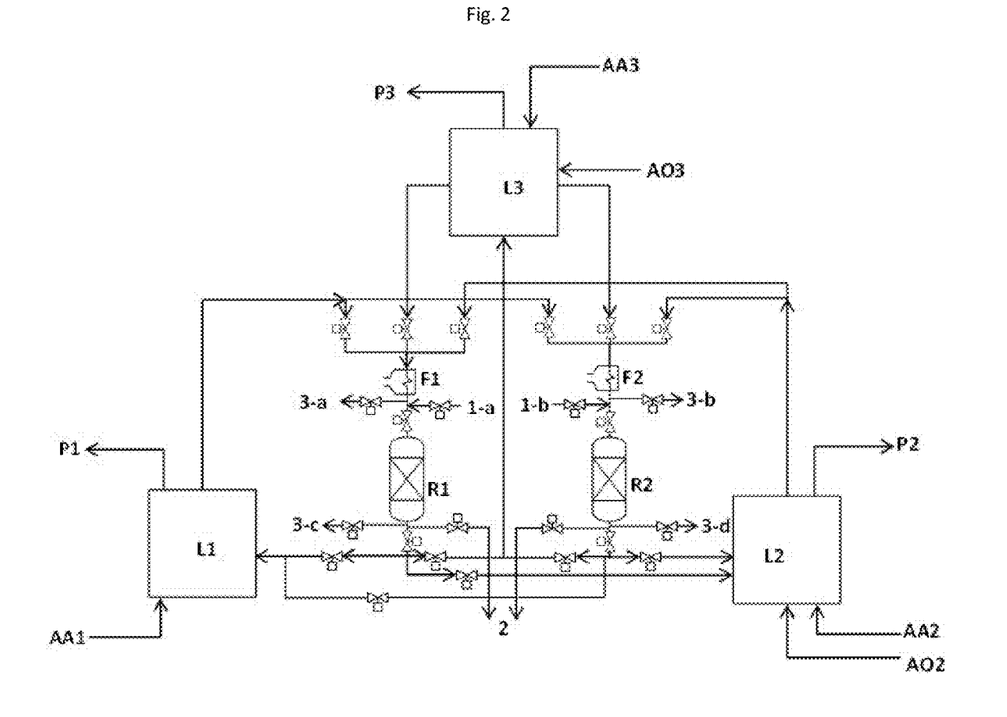
FIG. 2 shows the scheme of the regeneration step b2) in two reactors (R1) and (R2) in non-operational mode (i.e. in a multi-reactor system comprising six fixed-bed reactors), comprising three regeneration loops, a regeneration loop (L1) for the inert gas, a regeneration loop (L2) for the gas stream with a low oxygen content and a regeneration loop (L3) for the gas stream with a high oxygen content. Each regeneration loop (L1), (L2) and (L3) comprises a purge, (P1), (P2) and (P3), respectively. The regeneration loop (L1) for the inert gas (or stripping loop) also comprises a supply (AA1) of inert gas. The regeneration loop (L2) for the gas stream with a low oxygen content (or low $O_2$ loop) comprises a supply (AA2) of inert gas and a supply of dioxygen (AO2) (for example in the form of an air supply) and the regeneration loop (L3) for the gas stream with a high oxygen content (or high $O_2$ loop) also comprises a supply (AA3) of inert gas and a supply of dioxygen (AO3) (for example in the form of an air supply). Before the reactors (R1) and (R2), in a regeneration phase, the gas streams can be heated in ovens (F1) and (F2). The lines (3) (i.e. (3-a), (3-b), (3-c), (3-d)) correspond to safety offtakes. The lines (1) (i.e. (1-a), (1-b)) represent feed lines for ethanol/acetaldehyde feedstock for the reactors (R1) and (R2) when the latter are operational. The lines (2) represent the lines at the outlet of reactors (R1) and (R2) via which the reaction effluent produced is recovered to feed a separation section, for example.

The conversion into butadiene is carried out in 6 radial fixed-bed reactors, each containing a fixed bed of a catalyst based on tantalum oxide on a silica-based matrix, at 380° C. and 0.2 MPa and at a weight hourly space velocity (WHSV) of 2 $h^{-1}$. Supplies of ethanol and of acetaldehyde, obtained from purification and separation sections of the unconverted ethanol and acetaldehyde streams downstream of the reaction sections, are added to the ethanol/acetaldehyde effluent entering the second reaction unit, so that the total flow rate of ethanol/acetaldehyde mixture, at the inlet of the second reaction unit, is equal to 92.4 t/h. Under these conditions, the ethanol conversion is 34 mol % in reaction step 2 and the catalytic cycle of the catalyst based on tantalum oxide is 10 days. The six reactors function in parallel and in sequence as shown schematically in FIG. 1: each one starts the reaction phase with an offset of 5 days; at a given moment, 4 reactors are operational and 2 reactors are in the regeneration phase. The catalyst is regenerated in situ in each reactor according to the protocol presented in Table 1. The regeneration section comprises three regeneration loops:

a nitrogen loop for providing the nitrogen stream required for stripping the catalyst, a loop for the gas stream with a low content of $O_2$ making it possible to provide a gas stream comprising nitrogen and 0.5% by volume of $O_2$ and a loop for the gas stream with a low content of $O_2$ making it possible to provide a gas stream comprising nitrogen and 6.0% by volume of $O_2$.

TABLE 1

Regeneration protocol

| Period | Initial T, °C. | Final T, °C. | Ramp, °C./h | vol % O$_2$ | Stage time, h |
|---|---|---|---|---|---|
| I | 350 | 350 | — | 0.0 | 12 |
| II | 350 | 350 | — | 0.5 | 30 |
| III | 350 | 410 | 20 | 0.5 | 3 |
| IV | 410 | 410 | — | 0.5 | 16.5 |
| V | 410 | 410 | — | 6.0 | 19 |
| VI | 410 | 480 | 20 | 6.0 | 3.5 |
| VII | 480 | 480 | — | 6.0 | 20 |
| VIII | 480 | 350 | 100 | 0.0 | 1.5 |
| IX | 350 | 350 | — | 0.0 | 12 |

Table 2 indicates composition variations in the reaction effluent, over the duration of functioning.

TABLE 2

Composition variations in the reaction effluent

| Component | Variation, wt % |
|---|---|
| Ethanol | 0.8 |
| Acetaldehyde | 4.7 |
| Butadiene | 6.1 |
| Diethyl ether | 6.7 |

It appears that the composition variations of the reaction effluent that are observed at the reaction unit outlet are low. Over the duration of functioning of the process, the butadiene production shows flow rate variations of only 6% by weight.

Table 3 presents the consumptions of utilities for the regeneration of the tantalum oxide based catalyst, for all of the reactors, over the duration of functioning.

TABLE 3

Consumptions of utilities for the regeneration

| Nitrogen, Nm$^3$/h | 48.79 |
|---|---|
| Instrument Air, Nm$^3$/h | 317.19 |
| Electricity, kW | 2084.25 |
| Boiler water, t/h | 2.67 |
| Gas fuel, kW | 1923.95 |

The consumption of utilities for the regeneration step is relatively low. In particular, the nitrogen consumption (48.79 Nm$^3$/h) over the duration of functioning of the process remains very low in particular relative to the nitrogen consumption of a reactor system that is similar but with once-through regeneration (N$_2$ consumed=42 400 Nm$^3$/h).

Example 2 (in Accordance)

In this example, the second reaction unit comprises 6 (4+2) fixed-bed reactors and is operated at a weight hourly space velocity (WHSV) of 1.2 h$^{-1}$. The regeneration section comprises three regeneration loops.

The conversion of ethanol into acetaldehyde is carried out in a multitubular reactor comprising a catalyst based on copper oxide on a silica support, at 275° C. and 0.26 MPa. The ethanol/acetaldehyde effluent, which is separated from the hydrogen stream at the reactor outlet, is then sent to the second reaction unit.

The conversion into butadiene is carried out in six radial fixed-bed reactors, each containing a fixed bed of a catalyst based on tantalum oxide on a silica-based matrix, at 380° C. and 0.2 MPa and at a weight hourly space velocity (WHSV) of 1.2 h$^{-1}$. Supplies of ethanol and of acetaldehyde, obtained from the sections for purification and separation of the unconverted ethanol and acetaldehyde streams downstream of the reaction sections, are added to the ethanol/acetaldehyde effluent entering the second reaction unit, so that the total flow rate of ethanol/acetaldehyde mixture entering the second reaction unit is equal to 129.7 t/h. Under these conditions, the ethanol conversion is 23 mol % in the reaction step 2 and the catalytic cycle of the catalyst based on tantalum oxide is 10 days. The six reactors function in parallel and sequentially as represented schematically in FIG. 1: each starts the reaction phase with an offset of 5 days; at a given moment, four reactors are operational and two reactors are in the regeneration phase. The catalyst is regenerated in situ in each reactor according to the same protocol as that of Example 1 and presented in Table 1. The regeneration section comprises three regeneration loops:

a nitrogen loop for providing the nitrogen stream necessary for stripping the catalyst, a loop for a gas stream with a low O$_2$ content for providing a gas stream comprising nitrogen and 0.5 vol % and a loop for a gas stream with a low O$_2$ content for providing a gas stream comprising nitrogen and 6.0 vol % of O$_2$.

Table 4 indicates variations in composition in the reaction effluent.

TABLE 4

Variations of compositions in the reaction effluent

| Component | Variation, weight % |
|---|---|
| Ethanol | 0.8 |
| Acetaldehyde | 4.7 |
| Butadiene | 6.1 |
| Diethyl ether | 6.7 |

It appears that the variations in composition of the reaction effluent observed leaving a reaction unit are low, throughout the functioning. Over the duration of functioning of the process, the butadiene production has flow rate variations of only 6% by weight.

Table 5 shows the consumptions of utilities, for the regeneration of the catalyst based on tantalum oxide, of all of the reactors, over the duration of functioning.

TABLE 5

Consumptions of the utilities for the regeneration

| Nitrogen, Nm3/h | 59.69 |
|---|---|
| Instrument Air, Nm3/h | 787.89 |
| Electricity, kW | 4658.61 |
| Boiler water t/h | 3.80 |
| Gas fuel, kW | 4229.62 |

The consumption of utilities for the regeneration step is relatively low. In particular, the nitrogen consumption (59.69 Nm$^3$/h) over the duration of functioning of the process remains very low, in particular relative to the nitrogen consumption of a similar system of reactors but with a once-through regeneration (N$_2$ consumed=47 619 Nm$^3$/h).

Example 3 (not in Accordance)

In this example, the multi-reactor system comprises two reactors: one reactor is in operational mode while the second is in regeneration (non-operational) mode.

All the other reaction and regeneration parameters are similar to those of Example 1.

Table 6 indicates variations of compositions in the reaction effluent.

TABLE 6

Variations of compositions in the reaction effluent

| Component | Variation, weight % |
|---|---|
| Ethanol | 4.6 |
| Acetaldehyde | 22.6 |
| Butadiene | 29.3 |
| Diethyl ether | 27.4 |

It appears that the variations in composition of the reaction effluent are greater at the outlet of the unit with two reactors such as that in Example 3 (not in accordance) than those observed in the systems with six reactors described in Examples 1 and 2 (in accordance). The butadiene production, in the process described in Example 3, has variations of 30% by weight.

The invention claimed is:

1. A process for producing butadiene from ethanol, comprising at least the following steps:
  a) a step of converting ethanol into an effluent comprising ethanol and acetaldehyde, comprising at least one reaction section (A) fed with a stream comprising ethanol and operated in the presence of a catalyst (Ca) at a temperature of between 200 and 500° C., and at a pressure of between 0.1 and 1.0 MPa;
  b) a butadiene conversion step comprising at least one reaction-regeneration section in which simultaneously implemented are a reaction step and a regeneration step in (n+n/2) fixed-bed reactors, n being an integer equal to 4 or a multiple thereof, said (n+n/2) fixed-bed reactors each comprising at least one fixed bed of a catalyst (Cb), said (n+n/2) fixed-bed reactors functioning in parallel and in sequence so that said reaction step starts in each of said reactors with a time shift equal to a quarter of the catalytic cycle time of said catalyst (Cb), said reaction-regeneration section comprising three regeneration loops, and wherein, at a given moment:
    b1) said reaction step is operated in n of said fixed-bed reactors, n being an integer equal to 4 or a multiple thereof, fed at least with a fraction of said effluent obtained from step a), at a temperature of 300 to 400° C., at a pressure of between 0.1 and 1.0 MPa, and for a time equal to the catalytic cycle time of said catalyst (Cb), to produce a reaction effluent, and
    b2) said regeneration step is operated in n/2 of said fixed-bed reactors for a total time equal to half of the catalytic cycle time of said catalyst (Cb), and comprises the following four successive phases:
      i. a stripping phase operated at a temperature of 300 to 400° C., under a stream of inert gas, said phase i) starting on conclusion of the reaction step b1); and then
      ii. a first combustion phase operated on conclusion of phase i) under a gas stream comprising said inert gas and oxygen in a content of less than or equal to 1 vol % relative to the total volume of said gas stream, at a temperature of 300 to 450° C.; and then
      iii. a second combustion phase operated on conclusion of the first combustion phase ii) under a gas stream comprising said inert gas and oxygen in a content of greater than or equal to 2 vol % relative to the total volume of said gas stream, at a temperature of 390 to 550° C.; and then
      iv. a final stripping phase operated at a temperature of 300° C. to 550° C., under a stream of said inert gas;
    said three regeneration loops of said reaction-regeneration section comprising a regeneration loop for the inert gas of the stripping phases i) and iv), a regeneration loop for the gas stream of the first combustion phase ii) and a regeneration loop for the gas stream of the second combustion phase iii).

2. The process as claimed in claim 1, wherein the reaction section of step a) is operated at a temperature of 250° C. to 300° C., and at a pressure of 0.1 to 0.5 MPa.

3. The process as claimed in claim 1, wherein said fixed-bed reactors in said reaction step b1) are further fed with a supply of ethanol and/or a supply of acetaldehyde, and wherein a mole ratio of ethanol to acetaldehyde in said reaction step b1) is 1 to 5.

4. The process as claimed in claim 1, wherein the integer n is equal to 4.

5. The process as claimed in claim 1, wherein said reaction step b1) is operated at a temperature of 300 to 360° C.

6. The process as claimed in claim 1, wherein said reaction step b1) is operated at a pressure of 0.2 to 0.4 MPa.

7. The process as claimed in claim 1, wherein the catalytic cycle time of said catalyst (Cb) for the butadiene conversion step b) is greater than or equal to 1 day, and less than or equal to 20 days.

8. The process as claimed in claim 1, wherein the inert gas of the regeneration step b2) is nitrogen, carbon dioxide ($CO_2$) or a mixture thereof.

9. The process as claimed in claim 1, wherein said stripping phase i) is operated at a temperature of 330 to 370° C.

10. The process as claimed in claim 1, wherein a flow rate of inert gas of said stripping phase i) is 0.5 to 1.5 $Nm^3$/h/kg of catalyst.

11. The process as claimed in claim 1, wherein the oxygen content of said first combustion phase ii) is 0.1 to 1 vol %.

12. The process as claimed in claim 1, wherein said first combustion phase ii) is operated at a temperature of 330 to 430° C.

13. The process as claimed in claim 1, wherein said first combustion phase ii) is operated at a flow rate of gas stream of 1.7 to 2.5 $Nm^3$/h/kg of catalyst.

14. The process as claimed in claim 1, wherein the oxygen content of said second combustion phase iii) is 2 to 20 vol %.

15. The process as claimed in claim 1, wherein said second combustion phase iii) is operated at a constant temperature of 390 to 430° C. followed by a temperature increase ramp of 10 to 30° C/h and then a phase at a constant temperature of 460 to 510° C.

16. The process as claimed in claim 1, wherein said second combustion phase iii) is operated at a flow rate of gas stream of 1.2 to 1.8 $Nm^3$/h/kg of catalyst.

17. The process as claimed in claim 1, wherein said final stripping phase iv) is operated on a temperature decrease ramp of 50 to 150° C/h followed by a phase at a constant temperature of 300 to 400° C.

18. The process as claimed in claim 1, wherein said final stripping phase iv) is operated under a stream of said inert gas, at a flow rate of 0.5 to 1.5 $Nm^3$/h/kg of catalyst.

19. The process as claimed in claim 1, wherein the inert gas of the regeneration step b2) is nitrogen.

20. The process as claimed in claim 1, wherein said first combustion phase ii) is operated at a constant temperature of 330 to 370° C. followed by a temperature increase ramp of 10 to 30° C/h and then a phase at a constant temperature of 390 to 430° C.

\* \* \* \* \*